United States Patent
Beck et al.

(12) 
(10) Patent No.: US 6,358,935 B1
(45) Date of Patent: Mar. 19, 2002

(54) PRESERVED CYCLODEXTRIN-CONTAINING COMPOSITIONS

(75) Inventors: Gary J. Beck, Fullerton, CA (US); Edward D. S. Kerslake, Newport Beach, MA (US); Orest Olejnik, Coto De Caza, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/388,968

(22) Filed: Sep. 2, 1999

Related U.S. Application Data
(60) Provisional application No. 60/098,854, filed on Sep. 2, 1998.

(51) Int. Cl.[7] .................... A61K 31/715; A61K 31/724; A61K 7/32
(52) U.S. Cl. .......................................... 514/58; 424/65
(58) Field of Search .......................... 514/58; 424/76.1, 424/65

(56) References Cited

U.S. PATENT DOCUMENTS

| | | | |
|---|---|---|---|
| 4,383,992 A | 5/1983 | Lipari ........................ 424/238 |
| 4,470,965 A | 9/1984 | Wolf et al. .................... 424/80 |
| 4,728,509 A | 3/1988 | Shimizu et al. ............... 424/81 |
| 4,975,428 A | 12/1990 | Shell ........................ 514/230.5 |
| 5,051,402 A | 9/1991 | Kurihara et al. .............. 514/11 |
| 5,134,127 A | 7/1992 | Stella et al. .................. 514/58 |
| 5,227,372 A | 7/1993 | Folkman ...................... 514/58 |
| 5,332,582 A | 7/1994 | Babcock et al. ......... 424/78.04 |
| 5,362,758 A | 11/1994 | Ahmed ........................ 514/777 |
| 5,376,632 A | 12/1994 | Konings et al. ................ 514/8 |
| 6,106,738 A | * 8/2000 | Woo et al. .................. 252/89.1 |

FOREIGN PATENT DOCUMENTS

| | | |
|---|---|---|
| EP | 0119737 | 9/1984 |
| EP | 605203 | 7/1994 |
| JP | 2262518 | 4/1989 |
| JP | 3048655 | 7/1989 |
| WO | 9415582 | 7/1994 |
| WO | 9806381 | 2/1998 |
| WO | WOPCT9900025 | * 1/1999 |

OTHER PUBLICATIONS

Rajewsji et al, Journal of Pharma. Sciences, vol. 85, pp. 1142–1169No. 11, 11/1996.
Loftsson et al, Drug Devel. & Indust. Pharmacy, 18(13), 1477–1484, (1992).
Jansen et al, Lens & Eye Toxicity Research, 7(3&4), 459–468 (1990).

* cited by examiner

*Primary Examiner*—Shep K. Rose
*Assistant Examiner*—Donna Jagor
(74) *Attorney, Agent, or Firm*—Stout, Uxa Buyan & Mullins, LLP; Frank J. Uxa

(57) ABSTRACT

Compositions including a liquid medium, a cyclodextrin component and a preservative component which has a reduced tendency to being complexed with the cyclodextrin component. In one embodiment, the preservative component is a chlorite component. Active components, such as pharmaceutically active components or drugs, preferably are included in the compositions.

18 Claims, No Drawings

PRESERVED CYCLODEXTRIN-CONTAINING COMPOSITIONS

RELATED APPLICATION

This application claims benefit of Provisional Application Ser. No. 60/098,854 filed Sep. 2, 1998.

BACKGROUND OF THE INVENTION

The present invention relates to preserved cyclodextrin-containing compositions. More particularly, the invention relates to cyclodextrin-containing compositions, for example, such compositions containing one or more pharmaceutically active components, including preservatives which have substantial preserving efficacy in the presence of cyclodextrin components.

Cyclodextrins are widely known in the literature to increase the solubility of poorly water soluble pharmaceuticals or drugs and/or enhance pharmaceutical/drug stability and/or reduce unwanted side effects of pharmaceuticals/drugs. For example, steroids, which are hydrophobic, often exhibit an increase in water solubility of one order of magnitude or more in the presence of cyclodextrins. However, one substantial problem with pharmaceutical compositions including cyclodextrins, particularly such compositions in multi-dose formats, has to do with preserving such compositions. Typical preservatives are relatively ineffective at normal concentrations in such compositions, that is the compositions including such preservatives are unable to meet or pass standard preservative efficacy tests. It is believed that the preservative becomes complexed with the cyclodextrin and is rendered ineffective or has reduced effectiveness as a preservative.

It would be advantageous to provide cyclodextrin-containing compositions which are effectively preserved.

SUMMARY OF THE INVENTION

New cyclodextrin-containing compositions have been discovered. Such compositions include preservatives which are effective and efficacious in the presence of cyclodextrins. Preferably, the preservatives are present in the compositions in amounts to provide acceptable preservative efficacy and, in addition, are sufficiently innocuous or non-toxic so that the compositions can be administered to humans or animals to obtain desired therapeutic effects without significant detriment resulting from the presence of the preservatives. For example, the present compositions may include a pharmaceutical effective in providing a therapeutic effect when administered to the eyes of a human or animal. The preservative employed is preferably ophthalmically acceptable at the concentration employed so that the human or animal is effectively treated without significant harm caused by the presence of the preservative.

In short, the present compositions effectively take advantage of cyclodextrin components, e.g., in increasing the apparent water solubility of pharmaceuticals, and are effectively preserved and preferably substantially non-toxic in use.

In one broad aspect of the present invention, compositions are provided which comprise a liquid medium, a cyclodextrin component, for example, in an amount in the range of about 0.1% to about 30% (w/v), and a preservative component in an effective preserving amount, preferably of less than about 1% (w/v) or about 0.8% (w/v) and may be in the range of about 10 ppm(w/v) or less to about 200 ppm(w/v). In one embodiment, the preservative component has sufficient preservative efficacy so that the composition including such preservative component passes one or more standard preservative efficacy tests, such as in the United States Preservative Efficacy Test (USPET), the European Preservative Efficacy Test-A (EP-A), the European Preservative Efficacy Test-B (EP-B), and the like standard tests.

Preferably, the preservative component has an increased or greater preservative efficacy in the present composition relative to an identical amount (w/v) of benzalkonium chloride. Benzalkonium chloride, which is a preservative that is often used in pharmaceutical compositions, is relatively ineffective at typical concentrations in compositions including cyclodextrin component. It is believed that the benzalkonium chloride complexes with the cyclodextrin component. This complex renders the benzalkonium chloride antimicrobially ineffective. Thus, benzalkonium chloride has a reduced preservative efficacy in the presence of cyclodextrin component. More preferably, the present preservative component forms a complex with the cyclodextrin component, if at all, to a lesser extent than does benzalkonium chloride.

The present compositions preferably are substantially free of inclusion complexes of the cyclodextrin component and the preservative component.

Using a preservative component in accordance with the present invention which is substantially not affected by the cyclodextrin component allows the preservative component to be more efficacious as a preservative. Alternately, reduced amounts of the preservative component can be used to achieve acceptable preservative results. Such reduced amounts of preservative components reduce the toxicity or sensitivity for the composition as it is being administered to a human or animal.

Any suitable preservative component which functions as described herein is included within the scope of the present invention. The preservative efficacy tests identified herein are standard tests which can be easily and routinely conducted on any prospective preservative component to determine if such preservative component meets the criteria. Of course, the present preservative components should have no substantial detrimental effect on the composition or the active component or components of the composition or the use of the composition or the human or animal to whom the composition is administered. Tests to determine whether a prospective preservative component meets these criteria are well known and can be routinely conducted. In other words, one of ordinary skill in the art can determine, without undue experimentation, whether or not any prospective preservative component is within the scope of the preservative components of the present invention.

In one particularly useful embodiment, the present preservative component is selected from chlorite components, sorbic acid components and mixtures thereof present in an effective preserving amount. More preferably, the preservative component is selected from stabilized chlorine dioxide, alkali metal chlorites, sorbic acid, alkali metal sorbates and mixtures thereof. Chlorite components are very effective in the present compositions since they achieve preservative effectiveness at a relatively reduced concentration. Both the chlorite components and sorbic acid components are effective preservatives in the presence of cyclodextrin. Without wishing to limit the invention to any particular theory of operation, it is believed that the chlorite components and the sorbic acid components are substantially free in the presence of the cyclodextrin component or are substantially not complexed with the chlorodextrin component.

In another broad aspect of the present invention, compositions are provided which comprise a liquid medium, an active component, a cyclodextrin component and a preservative component. The active component is present in an amount effective in providing a desired effect to a human or an animal after the composition is administered to the human or animal. The cyclodextrin component preferably is present in an amount effective to increase the apparent solubility of the active component in the liquid medium and/or enhance the stability of the active component in the composition and/or reduce unwanted side effects of the acting component in the composition. The preservative component is present in an effective preserving amount, preferably less than about 1% (w/v) or about 0.8% (w/v) and may be in the range of about 10 ppm(w/v) or less to about 200 ppm(w/v). The preservative component is as identified elsewhere herein.

The present compositions which include active components, preferably pharmaceutically active components, as described herein, are particularly useful in multi-dose formats in which preservative efficacy is particularly important. Thus, such compositions obtain the advantages of cyclodextrin components, for example, in enhancing the solubility of the active components and, in addition, include effective preservative components, preferably at concentrations which reduce the risk of causing any substantial or significant harm or detriment to the humans or animals to whom the compositions are administered as a result of the presence of the preservative components.

Any feature or combination of features described herein are included within the scope of the present invention provided that the features included in any such combination are not mutually inconsistent.

Additional advantages and aspects of the present invention are apparent in the following detailed description and claims.

DETAILED DESCRIPTION

The present compositions include liquid media, cyclodextrin components, and preservative components. Preferably, the present compositions further include active components, more preferably pharmaceutically active components. The present compositions can have the characteristics of simple liquid, for example, aqueous liquid, solutions.

Any suitable cyclodextrin component may be employed in accordance with the present invention. The useful cyclodextrin components include, but are not limited to, those materials which are effective in increasing the apparent solubility, preferably water solubility, of poorly soluble active components and/or enhance the stability of the active components and/or reduce unwanted side effects of the active components. Examples of useful cyclodextrin components include, but are not limited to: α-cyclodextrin, derivatives of α-cyclodextrin, β-cyclodextrin, derivatives of β-cyclodextrin, γ-cyclodextrin, derivatives of γ-cyclodextrin, carboxymethyl-β-cyclodextrin, carboxymethyl-ethyl-β-cyclodextrin, diethyl-β-cyclodextrin, dimethyl-β-cyclodextrin, methyl-β-cyclodextrin, random methyl-β-cyclodextrin, glucosyl-β-cyclodextrin, maltosyl-β-cyclodextrin, hydroxyethyl-β-cyclodextrin, hydroxypropyl-β-cyclodextrin, sulfobutylether-β-cyclodextrin, and the like and mixtures thereof. As used herein, the term "derivatives" as it relates to a cyclodextrin means any substituted or otherwise modified compound which has the characteristic chemical structure of a cyclodextrin sufficiently to function as a cyclodextrin component, for example, to enhance the solubility and/or stability of active components and/or reduce unwanted side effects of the active components and/or to form inclusive complexes with active components, as described herein.

The specific cyclodextrin component selected should have properties acceptable for the desired application. The present compositions, and therefore the cyclodextrin component, may be applied topically and/or systemically. Topical application is preferred. In certain situations, the cyclodextrin component should have or exhibit reduced toxicity, particularly if the composition is to be exposed to sensitive body tissue, for example, eye tissue, etc. Very useful cyclodextrin components include β-cyclodextrin, derivatives of β-cyclodextrin and mixtures thereof. Particularly useful cyclodextrin components include sulfobutylether β-cyclodextrin, hydroxypropyl β-cyclodextrin and mixtures thereof. Sulfobutylether β-cyclodextrin is especially useful, for example, because of its substantially reduced toxicity.

The amount of cyclodextrin component in the present compositions is not of critical importance. Such amount should be effective to perform the desired function or functions in the present composition and/or after administration to the human or animal. The amount of cyclodextrin component preferably is sufficient to complex at least in major amount, and more preferably substantially all, of the active component in the present composition. In one useful embodiment, the amount of cyclodextrin component in the present composition is in the range of about 0.1% to about 30% (w/v) or more of the composition.

The present preservative components are selected so as to be effective and efficacious as preservatives in the present compositions, that is in the presence of cyclodextrin components, and preferably have reduced toxicity and more preferably substantially no toxicity when the compositions are administered to a human or animal.

As stated above, preservatives which are commonly used in pharmaceutical compositions are often less effective when used in the presence of cyclodextrins. In certain instances, this reduced preservative efficacy can be compensated for by using increased amounts of the preservative. However, where sensitive or delicate body tissue is involved, this approach may not be available since the preservative itself may cause some adverse reaction or sensitivity in the human or animal, to whom the composition is administered.

Preferably, the present preservative components are effective in concentrations of less than about 1% (w/v) or about 0.8% (w/v) and may be 500 ppm (w/v) or less, for example, in the range of about 10 ppm(w/v) or less to about 200 ppm(w/v). In one embodiment, the present preservative components have greater preservative efficacy in the composition relative to an identical amount (w/v) of benzalkonium chloride in the presence of the cyclodextrin component. Testing to determine comparative preservative efficacy is well known and can be routinely conducted. Preservative components in accordance with the present invention preferably include, but are not limited to, those which form complexes with the cyclodextrin component to a lesser extent than does benzalkonium chloride.

Very useful examples of the present preservative components include, but are not limited to, chlorite components, sorbic acid components and mixtures thereof.

Specific examples of chlorite components useful as preservatives in accordance with the present invention include stabilized chlorine dioxide (SCD), metal chlorites, such as alkali metal and alkaline earth metal chlorites, and the like and mixtures therefor. Technical grade (or USP grade) sodium chlorite is a very useful preservative component. The exact chemical composition of many chlorite components, for example, SCD, is not completely understood. The manufacture or production of certain chlorite components is described in McNicholas U.S. Pat. No. 3,278,447, which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc. An especially useful SCD is a product sold under the trademark Purogene® by Bio-Cide International, Inc.

Specific examples of sorbic acid components useful as preservatives in accordance with the present invention include sorbic acid itself, as well as pharmaceutically and/or ophthalmically acceptable sorbic acid derivatives and mixture thereof. Useful sorbic acid components include, but are not limited to, metal sorbates, such as alkali metal and alkaline earth metal sorbates, and the like and mixtures thereof. If a sorbic acid component is employed as a preservative in accordance with the present invention, the composition advantageously has a pH of less than about 7, for example in the range of about 3 or about 4 to less than 7. Such pH conditions increase the antimicrobial effectiveness of the sorbic acid component so that somewhat reduced concentrations of the sorbic acid component may be effectively employed. Of course, it is not essential that the composition have a pH of less than 7.

The preservative component may be included in the composition at a predetermined concentration, e.g., to provide an effective preserving amount of preservative component in the composition. For example, if a chlorite component is employed as a preservative in accordance with the present invention, the concentration of the chlorite component preferably is less than about 500 ppm (w/v), and more preferably is in the range of about 10 ppm (w/v) or less to about 200 ppm (w/v). If a sorbic acid component is employed as a preservative, the concentration of the sorbic acid component preferably is in the range of less than about 1% (w/v) or about 0.8% (w/v), and more preferably is in a range of about 0.05% (w/v) or less to about 0.8% (w/v).

The presently useful active components preferably are chosen to benefit from the presence of the cyclodextrin components. In general, the active components are provided with increased apparent solubility, preferably increased apparent water solubility, by the presence of the cyclodextrin components. Without wishing to limit the invention to any particular theory of operation, it is believed that the active components form inclusion or clathrate complexes with the cyclodextrin components.

Examples of the pharmaceutically active component which may be benefitted by the presence of cyclodextrin components in the present invention include, but are not limited to, diphenyl hydantoin, adiphenine, allobarbital, aminobenzoic acid, amobarbital, ampicillin, anethole, aspirin, azopropazone, azulene barbituric acid, beclomethasone, beciomethasone dipropronate, bencyclane, benzaldehyde, benzocaine, benzodiazepines, benzodiazepines, benzothiazide, betamethasone, betamethasone 17-valerate, bromobenzoic acid bromoisovalerylurea, butyl-p-aminobenzoate, chloralhydrate, chlorambucil, chloramphenicol, chlorobenzoic acid, chlorpromazine, cinnamic acid, clofibrate, coenzyme A, cortisone, cortisone acetate, cyclobarbital, cyclohexyl anthranilate, deoxycholic acid, dexamethasone, dexamethasone acetate, diazepam, digitoxin, digoxin, estradiol, flufenamic acid, fluccinolone acetonide, 5-fluorouracil, flurbiprogen, griseofulvin, guaiazulene, hydrocortisone, hydrocortisone acetate, ibuprofen, indican, indomethacin, iodine, ketoprofen, lankacidin-group antibiotics, mefenamic acid, menadione, mephobarbital, methbarbital, methicillin, metronidazole, mitomycin, nitrazepam, nitroglycerin, nitrosureas, paramethasone, penicillin, pentobarbital, phenobarbital, phenobarbitone, phenyl-butyric acid, phenyl-valeric acid, phenytoin, prednisolone, prednisolone acetate, prednisone, progesterone, propylparaben, proscillaridin, prostaglandin A series, prostaglandin B series, prostaglandin E series, prostaglandin F series, quinoline anti-microbials reserpine, spironolactone, sulfacetamide sodium, sulfonamide, androgens, including but not limited to testosterone, thalidomide, thiamine dilaurylsulphate, thiamphenicolpalmitate, thiopental, triamcinolone, vitamin A, vitamin D3, vitamin E, vitamin K3, and warfarin.

The complexes may be prepared by any method known in the art for the preparation of complexes of cyclodextrin components. For example, the active component and cyclodextrin component may be dissolved in water or an organic solvent (either miscible or immiscible with water). Convenient solvents include for example diethylether, tetrahydrofuran, dioxane, acetone, dimethylsulfoxide, dimethylformamide and lower aliphatic alcohols. Preferably the active component is dissolved in either water or a mixture of water and a water-miscible solvent such as methanol or ethanol. The active component may also be suspended in water.

After equilibrium is reached, the complex may be isolated by any suitable technique for example, lyophilization, evaporation of the solvent, precipitation, low temperature crystallization, or spray-drying. Cyclodextrin inclusion complexes may also be produced by physically grinding or kneading the cyclodextrin component and the active component with or without a small amount of solvent. The ratio of cyclodextrin component to active component used to prepare the complexes may be any convenient ratio but the cyclodextrin component preferably is used in a molar excess.

Benefits may be obtained by having the molar ratio of cyclodextrin component to active component in the range of about 10:1 to about 1:1 or less, preferably about 5:1 or about 3:1 or about 2:1 to about 1:1 or less and by using the methods and ratios described above. Complexes are conveniently obtained containing up to 20% w/w of the active component. However, in view of the low doses of the drug normally administered and the difficulty of preparing homogenous mixtures of active ingredient and excipients it may be desirable to prepare the complex with an excess of the cyclodextrin component present, for example, complexes containing in the order of about 0.001% to about 10% by weight of the active component.

The liquid media useful in the present invention are selected to have no substantial detrimental effect on the present compositions, on the use of the compositions or on the human or animal to whom the compositions are administered. The liquid media are preferably aqueous-based. One useful aqueous liquid medium is that derived from saline, for example, a conventional saline solution or a conventional buffered saline solution. The aqueous liquid medium preferably has a pH in the range of about 4 or about 6 to about 9 or about 10, more preferably about 6 to about 8. In one embodiment, liquid medium preferably has a ophthalmically acceptable tonicity level, for example, of at least about 200 mOsmol/kg, more preferably in the range of about 200 to about 600 mOsmol/kg.

In order to insure that the pH of the aqueous liquid medium is maintained within the desired range, the aqueous liquid medium may include at least one buffer component. It is preferred that the buffer component be inorganic. Alkali metal and alkaline earth metal buffer components are advantageously used in the present invention.

Any suitable ophthalmically acceptable tonicity component or components may be employed, provided that such component or components are compatible with the other ingredients of the liquid medium and do not have deleterious or toxic properties which could harm the human or animal to whom the present compositions are administered. Example of useful tonicity components include sodium chloride, potassium chloride, mannitol, dextrose, glycerin, propylene glycol and mixtures thereof. In one embodiment, the tonicity component is selected from inorganic salts and mixtures thereof.

The present compositions may conveniently be presented as solutions or suspensions in aqueous liquids or non-aqueous liquids, or as oil-in-water or water-in-oil liquid emulsions. The present compositions may include one or more additional ingredients such as diluents, flavoring agents, surface active agents, thickeners, lubricants, and the like, for example, such additional ingredients which are conventionally employed in compositions of the same general type.

The present compositions in the form of aqueous suspensions may include excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gun tragacanth and gun acacia; dispersing or wetting agents may be a naturally occurring phosphatide, for example, lecithin, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example, polyoxyethylene sorbitan mono-oleate, and the like and mixtures thereof. Such aqueous suspensions may also contain one or more coloring agents, one or more flavoring agents and one or more sweetening agents, such as sucrose, saccharin, and the like and mixtures thereof.

The present compositions in the form of oily suspensions may be formulated in a vegetable oil, for example, olive oil, sesame oil or coconut oil, or in a mineral oil such as liquid paraffin. Such suspensions may contain a thickening agent, for example beeswax, hard paraffin or cetyl alcohol. Sweetening agents, such as those set forth above, and flavoring agents may be added to provide a palatable oral preparation.

The present compositions may also be in the form of oil-in-water emulsions. The oily phase may be a vegetable oil, for example, olive oil or arachis oil, or a mineral oil, for example, liquid paraffin, and the like and mixtures thereof. Suitable emulsifying agents may be naturally-occurring gums, for example, gum acacia or gun tragacanth, naturally-occurring phosphatides, for example, soya bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate. The emulsions may also contain sweetening and flavoring agents.

The present compositions in the form of syrups and elixirs may be formulated with sweetening agents, for example, as described elsewhere herein. Such formulations may also contain a demulcent, and flavoring and coloring agents.

The specific dose level for any particular human or animal depends upon a variety of factors including the activity of the active component employed, the age, body weight, general health, sex, diet, time of administration, route of administration, rate of excretion, drug combination and the severity of the particular condition undergoing therapy.

The active component in the present compositions may be administered at dosage levels and dosage intervals required to achieve the desired therapeutic effect normally associated with the active component and the disease or condition state in absence of the cyclodextrin component.

The following non-limiting examples illustrate certain aspects of the present invention.

EXAMPLES 1 AND 2

Two (2) aqueous compositions were prepared by blending together the following components:

| Components | Composition 1 | Composition 2 |
|---|---|---|
| Sodium chloride | 0.62% (w/v) | 0.62% (w/v) |
| Potassium chloride | 0.14% (w/v) | 0.14% (w/v) |
| Calcium chloride (dihydrate) | 0.02% (w/v) | 0.02% (w/v) |
| Magnesium chloride (hexahydrate) | 0.006% (w/v) | 0.006% (w/v) |
| Sodium carboxymethylcellulose | 0.5% (w/v) | 0.5% (w/v) |
| Boric acid | 0.2% (w/v) | 0.2% (w/v) |
| Sodium borate (decahydrate) | 0.14% (w/v) | 0.14% (w/v) |
| Brimodine tartarate[1] | 0.2% (w/v) | 0.2% (w/v) |
| Stabilized chlorine dioxide[2] | 50 ppm (w/v) | 50 ppm (w/v) |
| Sulfobutylether β cyclodextrin | — | 1% (w/v) |
| Water, USP | Q.S. to volume | Q.S. to volume |
| pH | 7.4 | 7.4 |

[1]Tartarate of 5-bromo-6-(2-imidozolin-2-ylamino) quinoxaline
[2]Product sold by Bio-Cide International Inc., under the trademark PUROGENE ®

Each of these compositions was tested for preservative efficacy in accordance with (1) United States Preservative Efficacy Test (USPET) test criteria; (2) European Preservative Efficacy-A (EP-A) test criteria; and (3) European Preservative-B (EP-B) test criteria. These test criteria are well known and conventionally utilized to determine the preservative efficacy of any given preservative or preserved composition.

The test results for each of these compositions is set forth in the following table.

| Composition | USPET | EP-A | EP-B |
|---|---|---|---|
| 1 | Pass | Fail | Fail |
| 2 | Pass | Fail | Pass |

These test results show that Composition 1 passes the USPET test criteria, and fails the EP-A and EP-B test criteria. The EP-B criteria were failed marginally by Composition 1 against *C. Albicans*. It is believed that composition 1 may pass the EP-B test criteria upon retest.

Composition 2 passes both the USPET and the EP-B test criteria and fails only the more strict EP-A test criteria.

These results demonstrate that the presence of a cyclodextrin component (Composition 2) does not have any detrimental effect on the preservative efficacy of stabilized chlorine dioxide, a chlorite component. These results indicate that the stabilized chlorine dioxide remains free and effective as a preservative in Composition 2, rather than being complexed by the cyclodextrin component and thus inhibited in providing preservative efficacy.

Composition 2, in accordance with the present invention, is ophthalmically acceptable and effective in providing therapeutic effects resulting from the presence of the brimonidine tartarate. The presence of the cyclodextrin component in Composition 2 enhances the effective or apparent water solubility of the brimonidine tartarate, substantially without detrimentally causing increased toxicity, for example, when administered to a patient in need of the therapeutic effects provided by brimonidine tartarate.

EXAMPLES 3 TO 9

(Comparative)

A series of seven (7) aqueous compositions were prepared by blending together the following components:

| Composition | Benzalkonium Chloride | Hydroxybutyl β cyclodextrin | Water | pH |
|---|---|---|---|---|
| 3 | 50 ppm (w/v) | 20% (w/v) | Q.S. to vol. | 8.0 |
| 4 | 100 ppm (w/v) | 20% (w/v) | Q.S. to vol. | 8.0 |
| 5 | 50 ppm (w/v) | 10% (w/v) | Q.S. to vol. | 7.2 |
| 6 | 50 ppm (w/v) | 10% (w/v) | Q.S. to vol. | 8.0 |
| 7 | 50 ppm (w/v) | 10% (w/v) | Q.S. to vol. | 8.0 |
| 8 | 50 ppm (w/v) | — | Q.S. to vol. | 7.2 |
| 9 | 50 ppm (w/v) | — | Q.S. to vol. | 8.0 |

Each of these aqueous compositions was tested for preservative efficacy in accordance with the USPET test criteria. Results of these tests are summarized in the following table.

| Composition | USPET Results |
|---|---|
| 3 | Fail |
| 4 | Fail |
| 5 | Fail |
| 6 | Fail |
| 7 | Fail |
| 8 | Pass |
| 9 | Pass |

These test results indicate that benzalkonium chloride is ineffective as a preservative when used in compositions including cyclodextrin components. Without wishing to limit the invention to any particular theory of operation, it is believed that the cyclodextrin component complexes the benzalkonium chloride sufficiently to inhibit or even prevent the benzalkonium chloride from being an effective preservative.

These results are in substantial contrast to the results set forth in Examples 1 and 2 in which stabilized chlorine dioxide is shown to be an effective preservative with or without a cyclodextrin component.

EXAMPLES 10 TO 21

A series of twelve (12) aqueous compositions were prepared by blending together the following components:

| | Composition[1] | | | | | |
|---|---|---|---|---|---|---|
| | 10 | 11 | 12 | 13 | 14 | 15 |
| Prednisolone Acetate, w/v % | — | — | — | — | 0.1 | 0.1 |
| Sulfobutylether β-cyclodextrin, w/v % | — | — | 8.0 | 8.0 | 8.0 | 8.0 |
| Benzalkonium chloride, w/v % | 0.15 | .0075 | 0.15 | .0075 | 0.15 | .0075 |
| Stabilized chlorine dioxide[2], w/v % | — | — | — | — | — | — |
| | 16 | 17 | 18 | 19 | 20 | 21 |
| Prednisolone Acetate, w/v % | — | — | — | — | 0.1 | 0.1 |
| Sulfobutylether β-cyclodextrin, w/v % | — | — | 8.0 | 8.0 | 8.0 | 8.0 |
| Benzalkonium chloride, w/v % | — | — | — | — | — | — |
| Stabilized chlorine dioxide [2], w/v % | 0.15 | .0075 | 0.15 | .0075 | 0.15 | .0075 |

[1]Each of the compositions includes USP water in a quantity sufficient to equal 100% w/v.
[2]Product sold by Bio-Cide International Inc., under the trademark PUROGENE ®

Each of these compositions was tested for preservative efficacy in accordance with (1) United States Preservative Efficacy Test (USPET) test criteria; (2) European Preservative Efficacy-A (EP-A) test criteria; and (3) European Preservative-B (EP-B) test criteria.

The test results for each of these compositions is set forth in the following table.

| Composition | USPET | EP-A | EP-B |
|---|---|---|---|
| 10 | Pass | Pass | Pass |
| 11 | Pass | Pass | Pass |
| 12 | Fail | Fail | Fail |
| 13 | Fail | Fail | Fail |
| 14 | Fail | Fail | Fail |
| 15 | Fail | Fail | Fail |
| 16 | Pass | Fail | Fail |
| 17 | Pass | Fail | Fail |
| 18 | Pass | Fail | Fail |
| 19 | Pass | Fail | Fail |
| 20 | Pass | Fail | Fail |
| 21 | Pass | Fail | Fail |

Compositions 10 and 11, which include only benzalkonium chloride, pass all of the preservative efficacy criteria. On the other hand, compositions 12 to 15, which include benzalkonium chloride and the cyclodextrin fail all preservative efficacy criteria. The addition of prednisolone acetate does not help to increase the antimicrobial activity, except for the activity against *S. Aureus*. All of the solutions, that is Compositions 16 to 21, containing stabilized chlorine dioxide pass the USPET. Compositions containing only stabilized chlorine dioxide, that is Compositions 16 and 17, fail the EP-A and EP-B tests on fungi only. When the cyclodextrin is added to the compositions including stabilized chlorine dioxide, Compositions 18 to 21, the antimicrobial activity is decreased. Compositions containing stabilized chlorine dioxide, the cyclodextrin, and prednisolone acetate, Compositions 20 and 21, fail the EP-A and EP-B criteria for the fungi only. The compositions including stabilized chlorine dioxide only fail the EP-B test only for *A. Niger*.

Although the presence of the cyclodextrin component does result in a decrease in the antimicrobial activity of the compositions, the combination of the cyclodextrin component and stabilized chlorine dioxide, a chlorite component, passes the preservative efficacy tests passed by compositions including only stabilized chlorine dioxide. These results indicate that a substantial portion of the stabilized chlorine dioxide remains free or not complexed by the cyclodextrin and effective as a preservative rather than being complexed by the cyclodextrin component and thus inhibited in providing preservative efficacy.

EXAMPLES 22 TO 29

A series of eight (8) aqueous compositions were prepared by blending together the following components:

| | Composition[1] | | | |
|---|---|---|---|---|
| | 22 | 23 | 24 | 25 |
| Prednisolone Acetate, w/v % | 0.1 | 0.1 | 0.1 | 0.1 |
| Sulfobutylether β-cyclodextrin, w/v % | 8.0 | 8.0 | 8.0 | 8.0 |
| Benzalkonium chloride, w/v % | 0.15 | 0.15 | 0.15 | 0.15 |
| Stabilized chlorine dioxide[2], w/v % | — | — | — | — |
| Potassium sorbate, w/v % | .05 | .5 | — | — |
| Glycerin, w/v % | — | — | 2.0 | — |
| Propyl glycol, w/v % | — | — | — | 2.0 |
| | 26 | 27 | 28 | 29 |
| Prednisolone Acetate, w/v % | 0.1 | 0.1 | 0.1 | 0.1 |
| Sulfobutylether β-cyclodextrin, w/v % | 8.0 | 8.0 | 8.0 | 8.0 |
| Benzalkonium chloride, w/v % | — | — | — | — |
| Stabilized chlorine dioxide[2], w/v % | .0075 | .0075 | .0075 | .0075 |
| Potassium sorbate, w/v % | .05 | .5 | — | — |
| Glycerin, w/v % | — | — | 2.0 | — |
| Propyl glycol, w/v % | — | — | — | 2.0 |

[1]Each of the compositions includes USP water in a quantity sufficient to equal 100% w/v.
[2]Product sold by Bio-Cide International Inc., under the trademark PUROGENE ®

Each of these compositions was tested for preservative efficacy in accordance with (1) United States Preservative Efficacy Test (USPET) test criteria; (2) European Preservative Efficacy-A (EP-A) test criteria; and (3) European Preservative-B (EP-B) test criteria.

The test results for each of these compositions is set forth in the following table.

| Composition | USPET | EP-A | EP-B |
|---|---|---|---|
| 22 | Fail | Fail | Fail |
| 23 | Fail | Fail | Fail |
| 24 | Fail | Fail | Fail |
| 25 | Fail | Fail | Fail |
| 26 | Pass | Fail | Fail |
| 27 | Pass | Fail | Pass |
| 28 | Pass | Fail | Fail |
| 29 | Pass | Fail | Fail |

These results indicate that all benzylkonium chloride-containing compositions fail all of the USPET, EP-A and EP-B criteria.

With regard to compositions including stabilized chlorine dioxide, Compositions 26, 28 and 29 fail the EP-A and EP-B criteria because of either or both *C. albicans* and *A. niger* or just a niger. Each of these compositions pass the USPET criteria. Composition 27 shows interesting results. This composition fails the EP-A criteria for *C. albicans* and *A. niger*, but passes both USPET and EP-B criteria. Upon repeat of the test, the composition passes the EP-A criteria.

The potassium sorbate even has an effect on the benzalkonium chloride-containing composition, that is Composition 23. Composition 23 still fails the USPET criteria, but only because of *E. coli* and *A. niger*. Other samples fail because of *P. aerogenosa*. Thus, the potassium sorbate is providing enhanced preservative efficacy in compositions including benzalkonium chloride.

EXAMPLES 30 TO 33

A series of four (4) aqueous compositions were prepared by blending together the following components:

| | Composition[1] | | | |
|---|---|---|---|---|
| | 30 | 31 | 32 | 33 |
| Prednisolone Acetate, w/v % | — | 0.1 | 0.1 | 0.1 |
| Sulfobutylether β-cyclodextrin, w/v % | — | 8.0 | 8.0 | 8.0 |
| Stabilized chlorine dioxide[2], w/v % | .0075 | — | — | — |
| Potassium sorbate, w/v % | — | 0.5 | 0.5 | 0.5 |
| PH | 7.4 | 6.5 | 5.5 | 4.5 |

[1]Each of the compositions includes USP water in a quantity sufficient to equal 100% w/v.
[2]Product sold by Bio-Cide International Inc., under the trademark PUROGENE ®

Each of these compositions was tested for preservative efficacy in accordance with (1) United States Preservative Efficacy Test (USPET) test criteria; (2) European Preservative Efficacy-A (EP-A) test criteria; and (3) European Preservative-B (EP-B) test criteria.

The test results for each of these compositions is set forth in the following table.

| Composition | USPET | EP-A | EP-B |
|---|---|---|---|
| 30 | Pass | Fail | Fail |
| 31 | Pass | Fail | Fail |
| 32 | Pass | Fail | Pass |
| 33 | Pass | Pass | Pass |

These results indicate that cyclodextrin compositions including either stabilized chlorine dioxide or potassium sorbate pass the USPET criteria. In particular, Compositions 31, 32 an 33 include both potassium sorbate and the cyclodextrin and pass the USPET criteria. At somewhat reduced pHs, as shown in Compositions 32 and 33, compositions including potassium sorbate and cyclodextrin pass the EP-B criteria (Composition 32) and even the EP-B and EP-A criteria (Composition 33).

Without wishing to limit the invention to any particular theory of operation, it is believed that the cyclodextrin component does not complex the sorbate component sufficiently to inhibit the sorbate from acting as an effective preservative. Also, the sorbate at more acidic conditions is a more effective preservative component.

While this invention has been described with respect to various specific examples and embodiments, it is to be understood that the invention is not limited thereto and that it can be variously practiced with the scope of the following claims.

What is claimed is:

1. A composition comprising:
   a liquid medium;
   a cyclodextrin component in an amount in a range of about 0.1% to about 30% (w/v);
   a pharmaceutically active component in an amount effective in providing a desired therapeutic effect to a human or animal after the composition is administered to the human or animal; and
   a preservative component in an effective preserving amount, the preservative component having a greater preservative efficacy in the composition relative to an identical amount of benzalkonium chloride in an identical composition without the preservative component.

2. The composition of claim 1 wherein the preservative component forms a complex with the cyclodextrin component to a lesser degree than benzalkonium chloride.

3. The composition of claim 1 wherein the liquid medium is an aqueous liquid medium, and the preservative component is present in an amount of less than about 0.8% (w/v).

4. The composition of claim 1 wherein the preservative component is present in an amount in a range of about 10 ppm(w/v) to about 200 ppm(w/v).

5. The composition of claim 1 wherein the cyclodextrin component is selected from the group consisting of β-cyclodextrin, derivatives of β-cyclodextrin and mixtures thereof.

6. The composition of claim 1 wherein the preservative component is selected from the group consisting of chlorite components, sorbic acid components and mixtures thereof.

7. The composition of claim 1 wherein the preservative component is stabilized chlorine dioxide.

8. The composition of claim 1 wherein the preservative component is selected from the group consisting of sorbic acid, sorbates and mixtures thereof.

9. The composition of claim 1 which is free of inclusion complexes of the cyclodextrin component and the preservative component.

10. A composition comprising:
    a liquid medium;
    a pharmaceutically active component in an amount effective in providing a desired therapeutic effect to a human or an animal after the composition is administered to the human or animal;
    a cyclodextrin component in an amount effective to increase the apparent solubility of the pharmaceutically active component in the liquid medium or to enhance the stability of the pharmaceutically active component in the composition or to reduce unwanted side effects of the active component; and
    a preservative component in an effective preserving amount, the preservative component having greater preservative efficacy in the composition relative to an identical amount of benzalkonium chloride in an identical composition without the preservative component.

11. The composition of claim 10 wherein the liquid medium is an aqueous liquid medium.

12. The composition of claim 10 wherein the cyclodextrin component is selected from the group consisting of β-cyclodextrin, derivatives of β-cyclodextrin and mixtures thereof.

13. The composition of claim 10 wherein the cyclodextrin component is present in an amount in a range of about 0.1% to about 30% (w/v).

14. The composition of claim 10 wherein the preservative component forms a complex with the cyclodextrin component to a lesser degree than does benzalkonium chloride.

15. The composition of claim 10 wherein the preservative component is present in an amount of about 1% (w/v) or less.

16. The composition of claim 10 wherein the preservative component is present in an amount in a range of about 10 ppm(w/v) to about 200 ppm(w/v).

17. The composition of claim 10 wherein the preservative component is selected from the group consisting of chlorite components, sorbic acid components and mixtures thereof.

18. The composition of claim 17 wherein the preservative component is stabilized chlorine dioxide.

* * * * *

UNITED STATES PATENT AND TRADEMARK OFFICE
CERTIFICATE OF CORRECTION

PATENT NO. : 6,358,935 B1
DATED : March 19, 2002
INVENTOR(S) : Beck et al.

It is certified that error appears in the above-identified patent and that said Letters Patent is hereby corrected as shown below:

Column 6,
Line 1, the word "fluccinolone" should be -- flucinolone --.

Column 8,
Line 36, in Example 1, under pH for Composition 1, "7.4 7.4" should read -- 7.4 --.
Line 36, in Example 1, under pH for Composition 2, insert -- 7.4 --.

Signed and Sealed this

Twenty-second Day of June, 2004

JON W. DUDAS
*Acting Director of the United States Patent and Trademark Office*